United States Patent [19]

Hiratani

[11] Patent Number: 4,560,759
[45] Date of Patent: Dec. 24, 1985

[54] CATION CARRIER

[75] Inventor: Kazuhisa Hiratani, Ibaraki, Japan

[73] Assignee: Director-General of Agency of Industrial Science-Technology, Tokyo, Japan

[21] Appl. No.: 470,016

[22] Filed: Feb. 25, 1983

[30] Foreign Application Priority Data

Feb. 25, 1982 [JP] Japan .................................. 57-30134

[51] Int. Cl.$^4$ ........................................... C07D 215/26
[52] U.S. Cl. ...................................... 546/178; 423/2; 423/6; 423/24
[58] Field of Search ......................................... 546/178

[56] References Cited

U.S. PATENT DOCUMENTS 4,433,151  2/1984  Hiratani ............................... 546/178

Primary Examiner—Glennon H. Hollrah
Assistant Examiner—D. B. Springer
Attorney, Agent, or Firm—Stephen F. K. Yee

[57] ABSTRACT

A novel polyether having the following general formula:

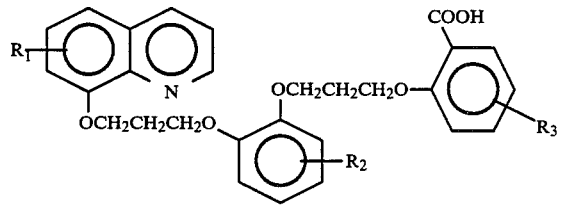

wherein $R_1$, $R_2$ and $R_3$ each stand for hydrogen or an alkyl group. The polyether can capture cations, especially alkali metal ions, when contacted with a cation-containing aqueous alkaline liquid and can release the cations to an aqueous acidic liquid, and thus serves as a cation carrier.

10 Claims, 1 Drawing Figure

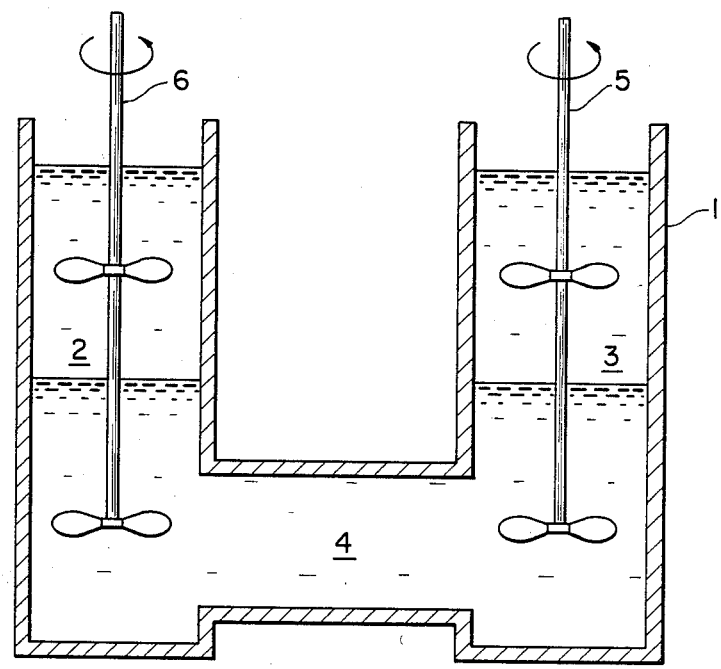

CATION CARRIER

BACKGROUND OF THE INVENTION

This invention relates to novel polyether derivatives useful as a carrier for transporting cations from one aqueous liquid to another aqueous liquid.

Concentration and extraction of cations such as metal ion become very important techniques in many fields such as biochemical and radiochemical arts. Especially, there is an increasing demand for a method for the selective separation of lithium which is utilized in a variety of fields such as for the production of tritium. Certain compounds such as 12-crown-4 and cryptate [2,1,1] are known to have a specific affinity to lithium ion and are proposed to be used for the separation of lithium ion. However, the known ether compounds are not satisfactory since lithium ion once captured by the ether compounds can not be easily released therefrom and since the separation of lithium ion by such ether compounds is greatly influenced by the kind of other coexisting cations.

SUMMARY OF THE INVENTION

It is an object of the present invention to provide novel polyether derivatives capable of capturing cations, especially alkali metal ions, in a cation-containing liquid and of liberating the captured cations to another liquid. Another object of this invention is to provide polyethers of the above-mentioned type with which the transportation of cations can be done at a high rate. It is a further object of this invention to provide a polyether of the above-mentioned type which can selectively transport lithium ion from a solution containing of lithium and other alkali metal ions. It is yet a further object of this invention to provide a polyether of the above-mentioned type which can transport cations from one cation-containing liquid to another cation-containing liquid, even when the concentration of the cations in the one liquid is lower than that in the other.

In accomplishing the foregoing objects, there is provided in accordance with the present invention a polyether having the following general formula (I):

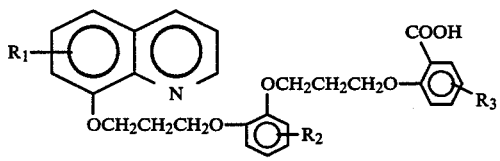

wherein $R_1$, $R_2$ and $R_3$ each stand for hydrogen or an alkyl group. The alkyl group preferably has 1 to 30 carbon atoms.

In another aspect, the present invention provides a method of transporting cations in a first liquid to a second liquid, which comprises contacting a third liquid, immiscible with the first and second liquids and containing the above polyether, with the first liquid so that the cations in the first liquid may be captured by the polyether, and contacting the third liquid containing the cations captured by the polyether with the second liquid so that the cations may be released to the second liquid.

Other objects, features and advantages of the present invention will become apparent from the detailed description of the invention to follow when considered in light of the accompanying drawing, in which the sole FIGURE is an elevational, cross-sectional view diagrammatically showing an apparatus useful for performing the cation transportation using the polyether of this invention.

DETAILED DESCRIPTION OF THE INVENTION

The polyether of this invention may be prepared any known manner. For example, a pyrocatechine derivative of the formula (II):

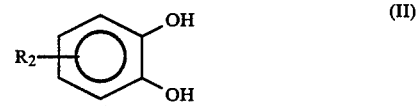

wherein $R_2$ has the same meaning as above, is reacted with 3-chloropropyl alcohol in an alkaline medium at a temperature of 60°–120° C. to form an ether. The treatment of the resultant ether with thionyl chloride in the presence of pyridine gives a compound (III):

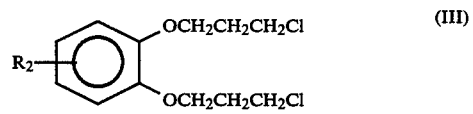

The compound (III) is subsequently reacted with an ester of the formula (IV):

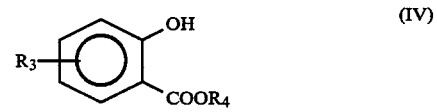

wherein $R_3$ has the same meaning as above and $R_4$ is a hydrocarbyl group, preferably an alkyl group of 1–4 carbon atoms, an aryl group such as phenyl, benzyl, tolyl or xylyl and an aralkyl group, in an alkaline medium at a temperature of 60°–120° C. to give a compound of the formula (V):

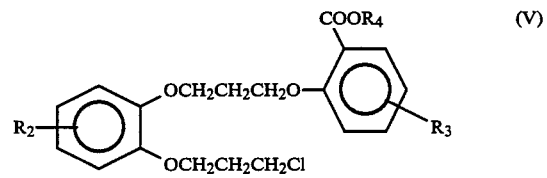

The resulting compound (V) is in turn reacted with an 8-quinolinol of the formula (VI):

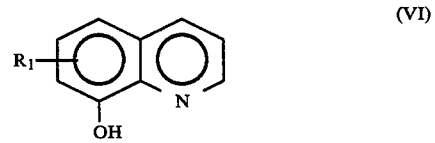

wherein $R_1$ has the same meaning as above, in an alkaline medium at a temperature of 30°–150° C., preferably 60°–120° C. to give a compound (VII):

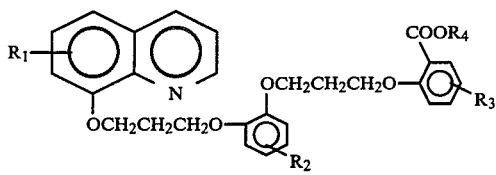

(VII)

The hydrolysis of the thus obtained product (VII) in an aqueous or alcohol solution containing an alkaline substance such as sodium hydroxide or potassium hydroxide at a temperature of 60°–80° C. and the washing of the resultant hydrolyzed product with an organic or inorganic acid gives the end polyether product of the formula (I).

The alkaline medium described above is a solution of an alkaline substance in a solvent inert to the alkaline substance. Illustrative of the inert solvents are dimethylformamide, hexamethylphosphoramide, dimethyl sulfoxide and n-butanol. Examples of the alkaline substances suitable for the formation of the alkaline medium include sodium hydride, sodium carbonate potassium carbonate, sodium hydroxide and potassium hydroxide.

The polyether according to this invention, when subjected to a pH region of about 8 to 13, can be in the form of carboxylate ($COO^-$) and can capture cations. It is presumed that not only the carboxylate but also the oxygen atoms of the ether linkages of the polyether interact with the cation to embrace the cations in the polyether molecules. At a pH in the range of about 1 to 6, the polyether can exist in the form of carboxylic acid (COOH) and can liberate the captured cations. Thus, the polyether can serve to act as a carrier for the transportation of cations. The polyether of this invention is particularly useful for transporting alkali metal ion.

The transportation of cations can be done by contacting a first, cation-containing liquid, generally an aqueous alkaline liquid preferably having a pH of about 8 to 13, with a third liquid, generally an organic solvent solution, containing the polyether of this invention and immiscible with the first liquid so that the cations may be captured by the polyether. Illustrative of the organic solvents are halogenated organic solvents such as chloroform, carbon tetrachloride and dichloroethane; hydrocarbons such as benzene, toluene, cyclohexane and n-hexane; and higher alcohols such as octanol and hexanol. The concentration of the polyether in the third liquid is generally in the range of $10^{-6}$ to $10^{-1}$ mol/l, preferably $10^{-5}$ to $10^{-2}$ mol/l. The third liquid thus containing the cations captured by the polyether is then contacted with a second liquid, generally an aqueous acidic liquid preferably having a pH of about 1 to 6, and immiscible with the third liquid so that the polyether changes into the form of carboxylic acid with the simultaneous liberation of the captured cations to the second liquid.

A preferred embodiment according to the present invention will now be described with reference to the accompanying drawing.

Referring to the FIGURE, designated by the reference numeral 1 is a U-shaped vessel equipped with stirrer means 5 and 6 in its respective vertical portions. The third, polyether-containing liquid is contained in the vessel 1 to form a third layer 4 with it liquid level positioned adjacent to the respective lower portions of the vertical portions. The first and second liquids are then poured into the vessel 1 to form first and second layers 2 and 3 on the third layer 4. In the interface at which the first and third layers 2 and 4 are contacted, the cations in the layer 2 are captured by the polyether contained in the layer 4, while in the interface at which the second and third layers 3 and 4 are contacted, the cations captured by the polyether are liberated and released to the second layer 3. The stirrer means 5 and 6 are continuously operated to facilitate the capture and the liberation of the cations. In this method, the third layer 4 should, of course, have a higher specific gravity than the other layers 2 and 3.

If desired, a suitable membrane may be disposed between the first and third liquids and between the second and third liquid. In a special case, the polyether may be supported on a suitable support means such as filter paper or high molecular weight membrane and each side of the polyether-supporting means is contacted with respective one of the first and the second liquids. The transportation may also be effected by usual extraction method in which the first and the third liquids are vigorously shaked together to extract the cation with the third liquid, the cation contained in the third liquid being subsequently extracted with the second liquid.

With the polyether according to this invention, the transportation of cations may be effected very fast. Further, even when the concentration of cations in the first liquid is lower than that in the second liquid, the polyether of this invention can carry the cations from the first to second liquids. The polyether of this invention is also featured in that it exhibits preference for alkali metals in the presence of other metal ions. The preference increases in the order: $Cs < K < Na < < Li$. For example, when ions of Li, Na, K, Cs, Rb, Ca, Mg, Sr, Fe, Cu, etc. are contained in the first liquid, the polyether selectively transports lithium ion.

The following examples will further illustrate the present invention.

EXAMPLE 1

16.6 g (0.1 mol) of 4-t-butylcatecol and 41 g (0.3 mol) of finely divided anhydrous potassium carbonate were mixed in 100 ml of dimethylformamide at 70° C. for 2 hours with stirring in the atmosphere of nitrogen. 20 g (0.21 mol) of 3-chloropropanol were then added to the mixture and heated at 70° C. for 7 days with stirring. After completion of the reaction, the reaction mixture was added with water. Solvent extraction was performed with chloroform and the chloroform layer was, after being washed thrice with water, dried over magnesium sulfate. Chloroform was then distilled off under vacuo and the residue was subjected to a vacuum distillation at 170° C. and 0.5 mmHg to give an ether (yield 41%). The ether was, after being dissolved in benzene, reacted with thionyl chloride in the presence of pyridine to give 1,2-bis(3'-chloropropyloxy)-4-t-butylbenzene with a yield of 87%.

6.6 g (0.021 mol) of the thus obtained ether were added to a mixture of 3.0 g (0.018 mol) of ethyl salicylate and 0.44 g (0.018 mol) of sodium hydride in 50 ml of dimethylformamide and the resulting mixture was reacted at 70° C. for 7 days with stirring. After completion of the reaction, water was added to the reaction mixture. Solvent extraction was performed with benzene and the benzene layer was, after being washed well with water, dried over anhydrous magnesium sulfate. Benzene was then distilled off, and the residue was heated at 150° C. under vacuo for the removal of unreacted materials. The remaining mass was subjected to column chromatography to obtain, with a yield of 76%, a mixed product (1:1) of 1-(3'-o-ethoxycarbonylphenoxypropyloxy)-2-(3'-chloropropyloxy)-4-t-butylbenzene and 1-(3'-o-ethoxycarbonylphenoxypropyloxy-2-(3'-chloropropyloxy)-5-t-butylbenzene.

4.8 g of the thus obtained product was added to a mixture of 2.0 g (0.014 mol) of 8-quinolinol and 0.30 g of sodium hydride dissolved in 30 ml of dimethylformamide, and the resulting mixture was reacted at 70° C. for 2 hours. Thereafter, water was added to the reaction mixture and the reaction product was extracted with benzene. The benzene layer, after being washed with water, was dried over magnesium sulfate and subjected to column chromatography to give 3.7 g of 1-(3'-o-ethoxycarbonylphenoxypropyloxy)-2-(3'-8"-quinolinoxypropyloxy)-4(or 5)-t-butylbenzene (yield:62%). The resultant ester was hydrolyzed in ethanol containing sodium hydroxide. By neutralizing the resulting mixture with acetic acid followed by the purification by column chromatography, there was quantitatively obtained a transparent, glassy solid product, 1-(3'-o-carboxylphenoxypropoxy)-2-(3'-8"-quinolineoxypropoxy)-4(or 5)-t-butylbenzene of the formulae (compound (I) in which $R_1$ is hydrogen, $R_2$ is t-butyl and $R_3$ is hydrogen):

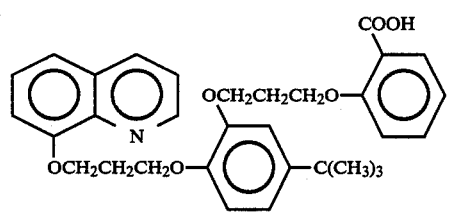

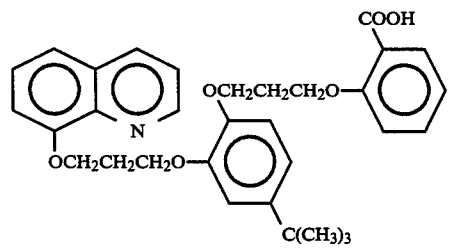

The structure of the polyether product was ellucidated from elementary analysis, IR, NMR and MS. The NMR spectrum of the polyether was as follows:

| | |
|---|---|
| 2.27 (ppm) | singlet, 9H, C—(CH$_3$)$_3$ |
| 2.0–2.77 | multiplet, 4H, OCH$_2$CH$_2$CH$_2$O |
| 4.07–4.66 | multiplet, 8H, OCH$_2$CH$_2$CH$_2$O |
| 6.87–7.73 | multiplet, 10H, aromatic proton |
| 8.20 | multiplet, 2H, aromatic proton |
| 9.09 | quadruplet, 1H, aromatic proton |
| c.a. 8.2 | broad,1H, COOH |

EXAMPLES 2–5

Example 1 was repeated in the same manner as that described in Example 1 except that catecol was used in place of 4-t-butylcatecol (Example 2), 4-octylcatecol was used in place of 4-t-butylcatecol (Example 3), ethyl 5-methylsalicylate was used in place of ethyl salicylate (Example 4), and ethyl 5-methylsalicylate and 7-methyl-8-quinolinol were used respectively in place of ethyl salicylate and 8-quinolinol (Example 5), whereby to give the following polyether compounds:

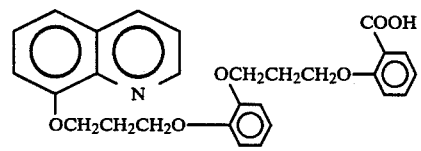
(Example 2)

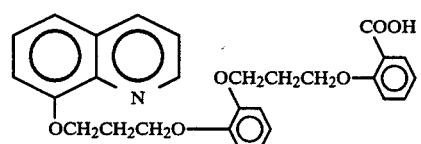
(Example 3)

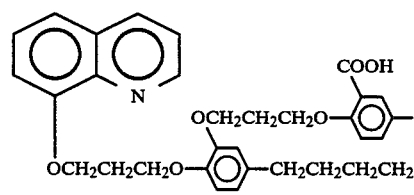
(Example 3)

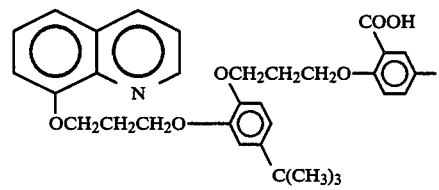
(Example 4)

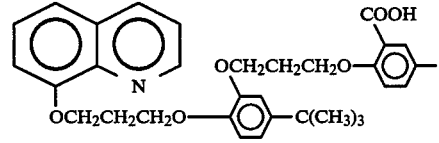
(Example 4)

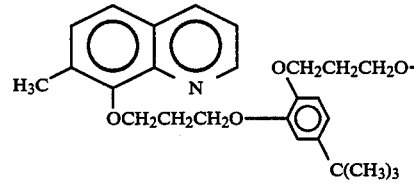
(Example 5)

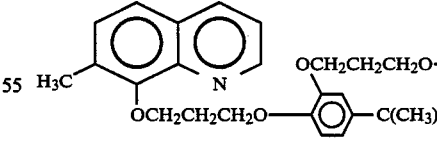
(Example 5)

EXAMPLE 6

Transportation of cation was conducted at 25° C. using an apparatus of the type shown in the FIGURE. The first, second and third liquids had the following formulations:

First liquid: 15 ml of an aqueous solution containing 0.1 mol/l of MOH

Second liquid: 15 ml of an aqueous solution containing 0.1 mol/l of MCl and 0.1 mol/l of HCl.

Third liquid:
Chloroform—30 ml
Mixed polyether product obtained in Example 1—1.5×10$^{-4}$ mols The amount of the cation M transported from the first liquid to the second liquid with the lapse of time was as shown in Table 1.

TABLE 1

| Experiment No. | Cation M | Amount of cation M transported (%)* | |
|---|---|---|---|
| | | 1 day | 2 days |
| 1 | Li | 40 | 54 |
| 2 | Na | 35 | 48 |
| 3 | K | 28 | 38 |

*Amount of cation M transported (%) = $\frac{\text{Amount of cation M increased in the second liquid}}{\text{Amount of cation M originally present in the first liquid}} \times 100 (\%)$

EXAMPLE 7

Transportation of cations was performed in the same manner as that in Example 6 except that the following liquids were used as the first and second liquids:

First liquid: 15 ml of an aqueous solution containing 0.1 mol/l of LiOH, 0.1 mol/l of NaOH, 0.1 mol/l of KOH and 0.1 mol/l of H$_2$SO$_4$(pH:12.4).

Second liquid: 15 ml of an aqueous solution containing 0.1 mol/l of LiOH, 0.1 mol/l of NaOH, 0.1 mol/l of KOH and 0.2 mol/l of H$_2$SO$_4$(pH:2.0).

The amount of each cation transported was as shown in Table 2.

TABLE 2

| Cation M | Amount of cation M transported (%) | |
|---|---|---|
| | 1 day | 2 days |
| Li | 33 | 41 |
| Na | 9 | 12 |
| K | 6 | 8 |

EXAMPLE 8

Example 7 was repeated using 0.2 mol/l of HCl in place of 0.1 mol/l of H$_2$SO$_4$ in the first liquid and 0.4 mol/l of HCl in place of 0.2 mol/l of H$_2$SO$_4$ in the second liquid. The results were as shown in Table 3.

TABLE 3

| Cation M | Amount of cation M transported (%) | |
|---|---|---|
| | 1 day | 2 days |
| Li | 20 | 30 |
| Na | 6 | 9 |
| K | 4 | 6 |

EXAMPLE 9

Example 7 was repeated using the following solutions as the first and second liquids:

First liquid: 15 ml of an aqueous solution containing 0.1 mol/l of NaOH, 0.1 mol/l of KOH, 0.1 mol/l of CsOH and 0.2 mol/l of HCl.

Second liquid: 15 ml of an aqueous solution containing 0.1 mol/l of NaOH, 0.1 mol/l of KOH, 0.1 mol/l of CsOH and 0.4 mol/l of HCl.

The amount of each cation transported was shown in Table 4.

TABLE 4

| Cation M | Amount of cation M transported (%) | |
|---|---|---|
| | 1 day | 2 days |
| Na | 12 | 19 |
| K | 6 | 9 |
| Cs | 2 | 4 |

EXAMPLE 10

Example 7 was repeated using the following solutions as the first and second liquids.

First liquid: 15 ml of an aqueous solution containing 0.15 mol/l of LiOH, 0.15 mol/l of NaOH, 0.15 mol/l of KOH and 0.175 mol/l of H$_2$SO$_4$.

Second liquid: 15 ml of an aqueous solution containing 0.15 mol/l of LiOH, 0.15 mol/l of NaOH, 0.15 mol/l of KOH and 0.275 mol/l of H$_2$SO$_4$.

The amount of each cation transported was as shown in Table 5.

TABLE 5

| Cation M | Amount of cation M transported (%) | |
|---|---|---|
| | 1 day | 2 days |
| Li | 17 | 24 |
| Na | 2 | 3 |
| K | <1 | 1 |

The results shown in Table 1 indicate that the polyether of this invention is effective in transporting alkali metal ion in an alkaline liquid to an acidic liquid even if the concentration of the alkali metal ion in the former liquid is lower than that in the latter. When several alkali metals coexist, the polyether selectively transport lithium ion, as will be appreciated from the results summarized in Tables 2-5.

I claim:

1. A polyether having the following general formula:

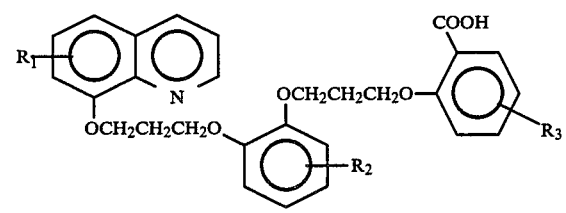

wherein R$_1$, R$_2$ and R$_3$ each stand for hydrogen or an alkyl group having from 1 to 30 carbon atoms.

2. A polyether according to claim 1 and having the formula:

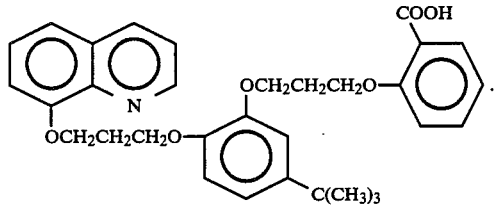

3. A polyether according to claim 1 and having the formula:

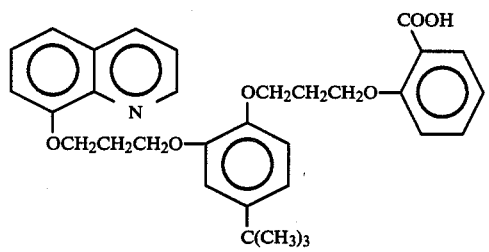

4. A polyether according to claim 1 and having the formula:

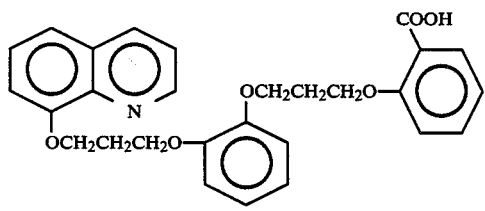

5. A polyether according to claim 1 and having the formula:

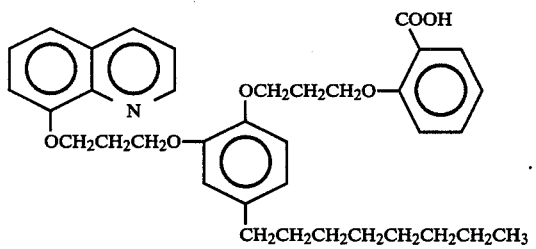

6. A polyether according to claim 1 and having the formula:

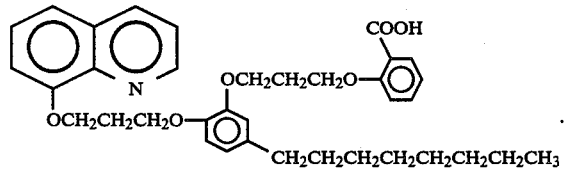

7. A polyether according to claim 1 and having the formula:

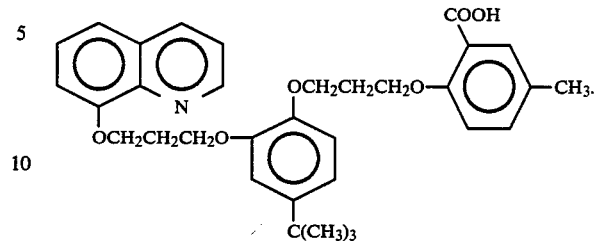

8. A polyether according to claim 1 and having the formula:

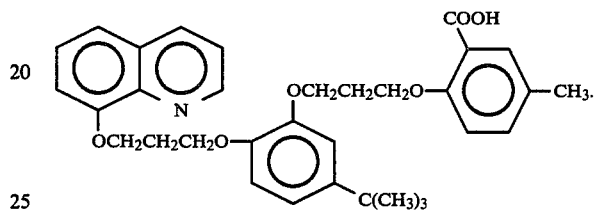

9. A polyether according to claim 1 and having the formula:

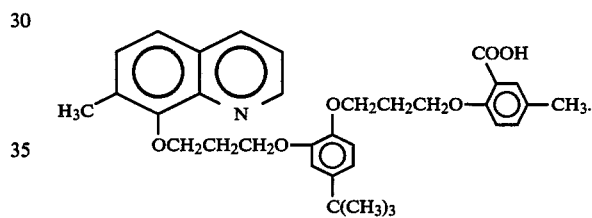

10. A polyether according to claim 1 and having the formula:

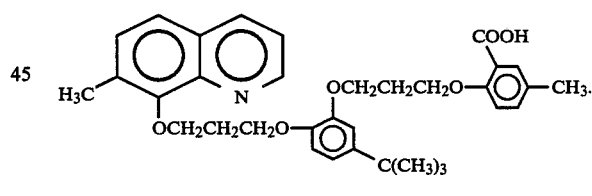

* * * * *